United States Patent
Bratz et al.

(10) Patent No.: US 6,514,910 B1
(45) Date of Patent: Feb. 4, 2003

(54) HERBICIDAL MIXTURE CONTAINING A 3-HETEROCYCLYL-SUBSTITUTED BENZOYL DERIVATIVE AND AN ADJUVANT

(75) Inventors: Matthias Bratz, Limburgerhof (DE); Rainer Berghaus, Speyer (DE); Martina Otten, Ludwigshafen (DE); Bernd Sievernich, Böhl-Iggelheim (DE); Elmar Kibler, Hassloch (DE); Herve Vantieghem, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/914,873
(22) PCT Filed: Feb. 28, 2000
(86) PCT No.: PCT/EP00/01641
§ 371 (c)(1), (2), (4) Date: Sep. 5, 2001
(87) PCT Pub. No.: WO00/53014
PCT Pub. Date: Sep. 14, 2000

(30) Foreign Application Priority Data

Mar. 5, 1999 (DE) .......................... 199 09 833

(51) Int. Cl.⁷ .................. A01N 43/78; A01N 43/80; A01N 25/30
(52) U.S. Cl. .................. 504/139; 504/266; 504/271
(58) Field of Search ................ 504/139, 266, 504/271

(56) References Cited

U.S. PATENT DOCUMENTS

| | | | |
|---|---|---|---|
| 4,834,908 A | 5/1989 | Hazen et al. | 252/356 |
| 4,966,728 A | 10/1990 | Hazen | 252/354 |
| 5,700,759 A | * 12/1997 | Caulder et al. | 504/133 |
| 5,846,907 A | 12/1998 | von Deyn et al. | 504/221 |

FOREIGN PATENT DOCUMENTS

| | | |
|---|---|---|
| CA | 2252543 | 11/1997 |
| EP | 356 812 | 3/1990 |
| WO | 92/06596 | 4/1992 |
| WO | 92/19107 | 12/1992 |
| WO | 96/26206 | 8/1996 |
| WO | 97/41116 | 6/1997 |
| WO | 97/41117 | 11/1997 |
| WO | 97/41118 | 11/1997 |

* cited by examiner

Primary Examiner—S. Mark Clardy
(74) Attorney, Agent, or Firm—Keil & Weinkauf

(57) ABSTRACT

A herbicidal mixture, comprising a) a herbicidally effective amount of a benzoyl compound of formula I

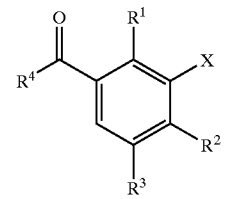

where:
$R^1$, $R^2$ are halogen, $C_1$–$C_6$-alkyl, $C_1$–$C_6$-alkylthio, $C_1$–$C_6$-alkyl-sulfinyl or $C_1$–$C_6$-alkylsulfonyl;
$R^3$ is hydrogen, halogen, $C_1$–$C_6$-alkyl;
X is 4,5-dihydroisoxazolyl which is unsubstituted or mono- or polysubstituted by halogen, $C_1$–$C_6$-alkyl, $C_1$–$C_4$-alkoxy, $C_1$–$C_4$-haloalkyl, $C_1$–$C_4$-haloalkoxy, $C_1$–$C_4$-alkylthio;
$R^4$ is a pyrazole of the formula II

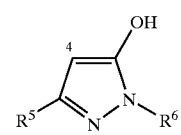

which is attached in the 4-position and where
$R^5$ is hydrogen,
$R^6$ is methyl,
or an environmentally compatible salt thereof;

b) an adjuvant comprising
i) a $C_1$–$C_5$-alkyl $C_5$–$C_{22}$-alkanoate,
ii) a $C_{10}$–$C_{20}$-carboxylic acid,
iii) a partial phosphoric ester or a partial sulfuric ester of a monohydroxy-functional polyalkyl ether and
iv) optionally an alkyl polyoxyalkylene polyether, wherein the compound of formula I and the adjuvat are present in synergistically effective amounts.

18 Claims, No Drawings

HERBICIDAL MIXTURE CONTAINING A 3-HETEROCYCLYL-SUBSTITUTED BENZOYL DERIVATIVE AND AN ADJUVANT

The present invention relates to a herbicidal mixture of a 3-heterocyclyl-substituted benzoyl derivative and an adjuvant, said mixture having synergistic action.

3-Heterocyclyl-substituted benzoyl derivatives are known and described, for example, in WO 96/26206, WO 97/41116, WO 97/41117 and Wo 97/41118.

EP-B-0584 227 discloses herbicidal compositions comprising substituted cyclohexanediones and nitrogen fertilizers.

The German-application P 19825588.8 discloses herbicidal mixtures based on a 3-heterocyclyl-substituted benzoyl derivative, a nitrogen-containing fertilizer and an adjuvant.

It is an object of the present invention to provide a herbicidal mixture which comprises 3-heterocyclyl-substituted benzoyl derivatives and whose herbicidal activity is higher than the activity of the pure active compound.

This object was achieved by a herbicidal mixture, comprising a) a herbicidally effective amount of a 3-heterocyclyl-substituted benzoyl derivative of the formula I

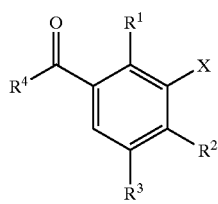

where:
$R^1, R^2$ are hydrogen, halogen, $C_1$–$C_6$-alkyl, $C_1$–$C_6$-alkylthio, $C_1$–$C_6$-alkylsulfinyl, $C_1$–$C_6$-alkylsulfonyl, $C_1$–$C_6$-haloalkyl, $C_1$–$C_6$-alkoxy, $C_1$–$C_6$-haloalkoxy;
$R^3$ is hydrogen, halogen, $C_1$–$C_6$-alkyl;
X is a heterocycle from the group consisting of isoxazolyl, 4,5-dihydroisoxazolyl and thiazolyl, where the heterocycle may be unsubstituted or mono- or polysubstituted by halogen, $C_1$–$C_6$-alkyl, $C_1$–$C_4$-alkoxy, $C_1$–$C_4$-haloalkyl, $C_1$–$C_4$-haloalkoxy, $C_1$–$C_4$-alkylthio;
$R^4$ is a pyrazole of the formula II

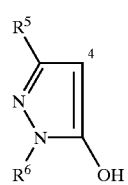

which is attached in the 4-position and where
$R^5$ is hydrogen or $C_1$–$C_6$-alkyl,
$R^6$ is $C_1$–$C_6$-alkyl,
or their environmentally compatible salts;
b) an adjuvant comprising
 i) a $C_1$–$C_5$-alkyl $C_5$–$C_{22}$-alkanoate,
 ii) a $C_{10}$–$C_{20}$-carboxylic acid,
 iii) a partial phosphoric ester or a partial sulfuric ester of a monohydroxy-functional polyalkyl ether and
 iv) if appropriate an alkyl polyoxyalkylene polyether in a synergistically effective amount.

The herbicidal mixture according to the invention displays a synergistic effect and is selective for those crop plants which are also compatible with the individual compounds.

With respect to the synergistic herbicidal action, particular preference is given to 3-heterocyclyl-substituted benzoyl derivatives of the formula Ib in which

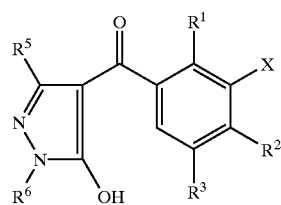

$R^1, R^2$ are chlorine, methyl, ethyl, $SCH_3$, $SOCH_3$, $SO_2CH_3$;
$R^3$ is hydrogen or methyl;
$R^5$ is hydrogen, methyl, trifluoromethyl;
$R^6$ is methyl, ethyl, isopropyl;
X is a heterocycle from the group consisting of: isoxazolyl, 4,5-dihydroisoxazolyl and thiazolyl, where the heterocycle may be unsubstituted or mono- or polysubstituted by halogen, $C_1$–$C_6$-alkyl, $C_1$–$C_4$-alkoxy, $C_1$–$C_4$-haloalkyl, $C_1$–$C_4$-haloalkoxy, $C_1$–$C_4$-alkylthio,
or their environmentally compatible salts.

Preferred compounds of the formula Ib are compiled in the table below:

| No. | $R^1$ | $R^2$ | $R^3$ | $R^5$ | $R^6$ | X |
|-----|-------|-------|-------|-------|-------|---|
| 1. | Cl | $SO_2CH_3$ | H | $CH_3$ | $CH_3$ | 2-thiazolyl |
| 2. | Cl | $SO_2CH_3$ | H | H | $CH_3$ | 2-thiazolyl |
| 3. | Cl | $SO_2CH_3$ | H | $CH_3$ | $CH_3$ | 4,5-dihydroisoxazol-3-yl |
| 4. | Cl | Cl | H | $CH_3$ | $CH_3$ | 4,5-dihydroisoxazol-3-yl |
| 5. | Cl | $SO_2CH_3$ | H | H | $CH_3$ | 4,5-dihydroisoxazol-3-yl |
| 6. | Cl | $SO_2CH_3$ | H | H | $CH_3$ | 4,5-dihydro-5-methylisoxa-zol-3-yl |
| 7. | Cl | $SO_2CH_3$ | H | H | $CH_3$ | 4,5-dihydro-5,5-dimethyl-isoxazol-3-yl |
| 8. | Cl | $SO_2CH_3$ | H | H | $CH_3$ | 4,5-dihydro-5-ethylisoxa-zol-3-yl |
| 9. | Cl | $SO_2CH_3$ | H | H | $CH_3$ | 4,5-dihydro-5,5-diethyl-isoxazol-3-yl |
| 10. | Cl | $SO_2CH_3$ | H | H | $CH_3$ | 4,5-dihydro-5-chloromethyl-isoxazol-3-yl |
| 11. | Cl | $SCH_3$ | H | H | $CH_3$ | 4,5-dihydroisoxazol-3-yl |
| 12. | Cl | $SO_2CH_3$ | H | H | $CH_3$ | 4,5-dihydro-5-ethoxyisoxa-zol-3-yl |
| 13. | Cl | $SO_2CH_3$ | H | H | $CH_3$ | 4,5-dihydro-5-methoxyisoxa-zol-3-yl |
| 14. | $CH_3$ | $SO_2CH_3$ | H | H | $CH_3$ | 4,5-dihydroisoxazol-3-yl |
| 15. | Cl | $SO_2CH_3$ | H | H | $CH_3$ | 4,5-dihydro-4,5-dimethyl-isoxazol-3-yl |
| 16. | Cl | $SO_2CH_3$ | H | H | $CH_3$ | 4,5-dihydro-5-thioethyl-isoxazol-3-yl |
| 17. | Cl | $SO_2CH_3$ | H | H | $CH_3$ | 4,5-dihydro-5-trifluoro-methylisoxazol-3-yl |
| 18. | $SCH_3$ | $SCH_3$ | H | H | $CH_3$ | 4,5-dihydroisoxazol-3-yl |
| 19. | Cl | $SO_2CH_3$ | H | H | $C_2H_5$ | 2-thiazolyl |
| 20. | Cl | $SO_2CH_3$ | H | H | $C_2H_5$ | 4,5-dihydroisoxazol-3-yl |
| 21. | Cl | $SO_2CH_3$ | H | H | $C_2H_5$ | 4,5-dihydro-5-methylisoxa-zol-3-yl |
| 22. | Cl | $SO_2CH_3$ | H | H | $C_2H_5$ | 4,5-dihydro-5,5-dimethyl-isoxazol-3-yl |

-continued

| No. | R¹ | R² | R³ | R⁵ | R⁶ | X |
|---|---|---|---|---|---|---|
| 23. | Cl | SO₂CH₃ | H | H | C₂H₅ | 4,5-dihydro-5-ethylisoxazol-3-yl |
| 24. | Cl | SO₂CH₃ | H | H | C₂H₅ | 4,5-dihydro-5,5-diethyl-isoxazol-3-yl |
| 25. | Cl | SCH₃ | H | H | C₂H₅ | 4,5-dihydroisoxazol-3-yl |
| 26. | Cl | SO₂CH₃ | H | H | C₂H₅ | 4,5-dihydro-5-chloromethyl-isoxazol-3-yl |
| 27. | Cl | SO₂CH₃ | H | H | C₂H₅ | 4,5-dihydro-5-ethoxyisoxa-zol-3-yl |
| 28. | Cl | SO₂CH₃ | H | H | C₂H₅ | 4,5-dihydro-4,5-dimethyl-isoxazol-3-yl |
| 29. | CH₃ | SO₂CH₃ | H | H | C₂H₅ | 4,5-dihydroisoxazol-3-yl |
| 30. | Cl | SO₂CH₃ | H | H | C₂H₅ | 4,5-dihydro-5-thioethyl-isoxazol-3-yl |
| 31. | Cl | SO₂CH₃ | H | H | C₂H₅ | 4,5-dihydro-5-trifluorome-thylisoxazol-3-yl |
| 32. | SCH₃ | SCH₃ | H | H | C₂H₅ | 4,5-dihydroisoxazol-3-yl |
| 33. | Cl | SO₂CH₃ | H | H | i-C₄H₉ | 4,5-dihydroisoxazol-3-yl |
| 34. | Cl | SO₂CH₃ | H | H | CH₃ | 3-methylisoxazol-5-yl |
| 35. | Cl | SO₂CH₃ | H | H | C₂H₅ | 3-methylisoxazol-5-yl |
| 36. | CH₃ | SO₂CH₃ | H | H | C₂H₅ | 3-methylisoxazol-5-yl |
| 37. | CH₃ | SO₂CH₃ | H | CH₃ | CH₃ | 4,5-dihydroisoxazol-3-yl |
| 38. | CH₃ | Cl | H | CH₃ | CH₃ | 4,5-dihydroisoxazol-3-yl |
| 39. | CH₃ | SO₂CH₃ | H | H | CH₃ | 4,5-dihydro-5-methylisoxa-zol-3-yl |
| 40. | CH₃ | SO₂CH₃ | H | H | CH₃ | 4,5-dihydro-5,5-dimethyl-isoxazol-3-yl |
| 41. | CH₃ | SO₂CH₃ | H | H | CH₃ | 4,5-dihydro-5-ethyl-isoxazol-3-yl |
| 42. | CH₃ | SO₂CH₃ | H | H | CH₃ | 4,5-dihydro-5,5-ethyl-isoxazol-3-yl |
| 43. | CH₃ | SO₂CH₃ | H | H | CH₃ | 4,5-dihydroisoxazol-3-yl |
| 44. | CH₃ | SO₂CH₃ | H | H | CH₃ | 4,5-dihydro-4,5-dimethyl-isoxazol-3-yl |
| 45. | CH₃ | Cl | H | H | C₂H₅ | 4,5-dihydroisoxazol-3-yl |
| 46. | CH₃ | SO₂CH₃ | H | H | C₂H₅ | 4,5-dihydro-5-methylisoxa-zol-3-yl |
| 47. | CH₃ | SO₂CH₃ | H | H | C₂H₅ | 4,5-dihydro-5,5-dimethyl-isoxazol-3-yl |
| 48. | CH₃ | SO₂CH₃ | H | H | C₂H₅ | 4,5-dihydro-5-ethyl-isoxazol-3-yl |
| 49. | CH₃ | SO₂CH₃ | H | H | C₂H₅ | 4,5-dihydro-4,5-dimethyl-isoxazol-3-yl |
| 50. | CH₃ | SO₂CH₃ | H | H | i-C₄H₉ | 4,5-dihydroisoxazol-3-yl |

Very particular preference is given to the compounds

4-[2-chloro-3-(4,5-dihydroisoxazol-3-yl)-4-methylsulfonylbenzoyl]-1-methyl-5-hydroxy-1H-pyrazole, 4-[2-methyl-3-(4,5-dihydroisoxazol-3-yl)-4-methylsulfonylbenzoyl]-1-methyl-5-hydroxy-1H-pyrazole, 4-[2-chloro-3-(3-methylisoxazol-5-yl)-4-methylsulfonylbenzoyl]-1-methyl-5-hydroxy-1H-pyrazole and/or their environmentally compatible salts.

Suitable environmentally compatible salts are, for example, salts of alkali metals, alkaline earth metals, ammonia or amines.

Suitable adjuvants b) comprise a mixture of
i) a $C_1$–$C_5$-alkyl $C_5$–$C_{22}$-alkanoate,
ii) a $C_{10}$–$C_{20}$-carboxylic acid,
iii) a partial phosphoric ester or a partial sulfuric ester of a monohydroxy-functional polyalkyl ether and
iv) if appropriate an alkyl polyoxyalkylene polyether.

These adjuvants are described, for example, in U.S. Pat. No. 4,834,908, EP 356 812 and EP 553 074.

Suitable $C_1$–$C_5$-alkyl $C_5$–$C_{22}$-alkanoates (i) are alkyl esters of a carboxylic acid, where the carboxylic acid contains 5–22 carbon atoms and the alkanol used for esterification contains 1–5 carbon atoms, such as, for example, methyl oleate, palmitate, myristate, linolenate, laurate, stearate, pelargonate, ethyl oleate, palmitate, myristate, linolenate, linoleate, laurate, stearate, pelargonate, n-propyl oleate, palmitate, myristate, linolenate, linoleate, laurate, stearate, pelargonate, isopropyl oleate, palmitate, myristate, linolenate, linoleate, laurate, stearate, pelargonate, n-butyl oleate, palmitate, myristate, linolenate, linoleate, laurate, stearate, pelargonate, isobutyl oleate, palmitate, myristate, linolenate, linoleate, laurate, stearate, pelargonate, n-pentyl oleate, palmitate, myristate, linolenate, linoleate, laurate, stearate, pelargonate. Preference is given to methyl oleate, methyl palmitate, ethyl oleate and mixtures thereof.

Suitable $C_{10}$–$C_{20}$-carboxylic acids (ii) include saturated and mono- and polyunsaturated carboxylic acids, such as, for example, oleic acid, palmitic acid, myristic acid, linoleic acid, linolenic acid, lauric acid and stearic acid. Preference is given to oleic acid.

Suitable partial phosphoric esters and partial sulfuric esters of a monohydroxy-functional polyalkylene ether (iii) are those whose polyalkylene ether radicals can be prepared by oxalkylation of long-chain alcohols such as $C_{10}$–$C_{20}$-alkanols, preferably $C_{10}$–$C_{16}$-alkanols, with alkylene oxides such as ethylene oxide, propylene oxide or butylene oxide. The alkylene oxides can be employed as a mixture, or else successively, for preparing block copolymers.

Preference is given to polyalkylene ethers having a $C_{10}$–$C_{16}$-alkyl chain with 10–15 mol of ethylene oxide units and 1–10, preferably 2–6, mol of propylene oxide units.

Preferred products are Klearfac™ AA 270 of BASF Corporation and Lutensit® A-EP from BASF Aktiengesellschaft.

If appropriate, it is possible to use alkyl polyoxyalkylene polyethers concomitantly. Suitable alkyl polyoxyalkylene polyethers are those which can be prepared by oxalkylation of $C_{10}$–$C_{25}$-alkanols with alkylene oxides such as ethylene oxide, propylene oxide or butylene oxide.

Preference is given to alkyl polyoxyalkylene polyethers having a $C_{10}$–$C_{25}$-alkyl chain, preferably $C_{12}$–$C_{20}$-alkyl chain, with an EO/PO block copolymer, such as, for example, Antarox® BO, Rhodia
Emulsogen® V 2436, Clariant
Plurafac® LF, BASF AG
Dehypon® LS, Henkel
Dehypon® LT, Henkel
Synperionic® LF, ICI Speciality Chemicals.

Particular preference is given to Plurafac® LF 700, BASF AG.

The adjuvant b) comprises the components in the following concentrations:

5 to 90% of the $C_1$–$C_5$-alkyl $C_5$–$C_{22}$-alkanoate,
2 to 40% of the $C_{10}$–$C_{20}$-carboxylic acid,
4 to 40% of the partial phosphoric ester or the partial sulfuric ester of a monohydroxy-functional polyalkyl ether and
0 to 75% of the alkyl polyoxyalkylene polyether.

Preference is given to:
5 to 60% of the $C_1$–$C_5$-alkyl $C_5$–$C_{22}$-alkanoate,
2 to 40% of the $C_{10}$–$C_{20}$-carboxylic acid, 5 to 35% of the partial phosphoric ester or the partial sulfuric ester of a monohydroxy-functional polyalkyl ether and 0 to 70% of the alkyl polyoxyalkylene polyether.

Particular preference is given to:

5 to 40% of the $C_1$–$C_5$-alkyl $C_5$–$C_{22}$-alkanoate, 2 to 35% of the $C_{10}$–$C_{20}$-carboxylic acid, 5 to 30% of the partial phosphoric ester or the partial sulfuric ester of a monohydroxy-functional polyalkyl ether and 0 to 70% of the alkyl polyoxyalkylene polyether.

The herbicidal mixture according to the invention comprises the components a) and b) in the following amounts:

0.5 to 90% by weight of the 3-heterocyclyl-substituted benzoyl derivative a);

10 to 99.5% by weight of the adjuvant b).

Preferred ratios are:

1 to 80% by weight of the 3-heterocyclyl-substituted benzoyl derivative a);

20 to 99% by weight of the adjuvant b).

Here, the components together are 100% by weight.

The individual components a) and b) of the herbicidal mixture according to the invention can be formulated and packaged together or individually.

The farmer employs the herbicidal mixture or its individual components for use in the spray tank.

To this end, the herbicidal mixture is diluted with water, it being possible, if appropriate, to add other auxiliaries and additives. However, the farmer himself can also mix the individual components a) and b) of the herbicidal mixture according to the invention in the spray tank and add, if appropriate, other auxiliaries and additives (tank mix method).

In the tank mix method, the components a) and b) are mixed in the spray tank and diluted to the desired use concentration using water.

For better processability, it is possible to add further auxiliaries and additives. The following components have been found to be useful auxiliaries and additives:

Solvents, antifoams, buffer substances, thickeners, spreading agents, compatibility-promoting agents.

Examples and brands of adjuvants and auxiliaries and additives are described in Farm Chemicals Handbook 1997; Meister Publishing 1997 p. C10 "adjuvant" or 1998 Weed Control Manual p. 86.

The mixture according to the invention is suitable as a herbicide. The herbicidal mixture controls vegetation on non-crop areas very efficiently, especially at high rates of application. It acts against broad-leaved weeds and weed grasses in crops such as wheat, rice, maize, soya and cotton without causing any significant damage to the crop plants. This effect is mainly observed at low rates of application.

Depending on the application method in question, the herbicidal mixture can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the herbicidal mixture can also be used in crops which tolerate the action of herbicides owing to breeding, including genetic engineering methods.

The herbicidal mixture can be applied pre- or post-emergence. If the herbicidal mixture is less well tolerated by certain crop plants, application techniques may be used in which the herbicidal mixture is sprayed, with the aid of the spraying equipment, in such a way that it comes into as little contact as possible, if any, with the leaves of the sensitive crop plants, while the herbicidal mixture reaches the leaves of undesirable plants growing underneath, or the bare soil surface (post-directed, lay-by).

The herbicidal mixture can be used, for example, in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading or pouring. The use forms depend on the intended aims; in any case, they should ensure the finest possible distribution of the herbicidal mixture according to the invention.

Suitable inert additives are essentially: mineral oil fractions of medium to high boiling point, such as kerosene and diesel oil furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols, such as methanol, ethanol, propanol, butanol and cyclohexanol, ketones such as cyclohexanone, strongly polar solvents, for example amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the herbicidal mixture, either as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which concentrates are suitable for dilution with water.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the herbicidal mixture together with a solid carrier.

Granules, for example coated granules, impregnated granules and homogeneous granules, can be prepared by binding the herbicidal mixture to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic minerals, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the herbicidal mixture in the ready-to-use preparations can be varied within wide ranges. In general, the formulations comprise approximately from 0.001 to 98% by weight, preferably 0.01 to 95% by weight, of the herbicidal mixture.

The mixture of the adjuvant b) can be formulated, for example, as shown in Table 2:

TABLE 2

| Component/Mixture No.: | No. 1 | No. 2 | No. 3 | No. 4 | No. 5 | No. 6 |
|---|---|---|---|---|---|---|
| C-65 Methyl ester[1] | 37 | 30 | 10 | 35 | 5 | 37 |
| Klearfac ® AA 270[2] | 7 | 15 | 15 | 2 | 7.5 | 22 |
| Lutensit ® A-EP[4] | | | | 25 | | |
| Oleic acid | 5 | 35 | | 5 | | 5 |
| Plurafac ® LF 700[3] | | | 75 | | 37.5 | |
| Silicone antifoam emulsion[5] | | | | 0.5 | | 0.5 |
| Solvesso ® 150[6] | 51 | 20 | | 34.5 | 50 | 35.5 |

[1])1:1 Mixtures of methyl oleate/methyl palmitate (Witco)
[2])Phosphate of a fatty acid alcohol ethoxylate/propoxylate (BASF Corporation)
[3])Fatty acid alcohol ethoxylate/propoxylate (BASF AG)
[4])Phosphate of a fatty acid alcohol ethoxylate/propoxylate (BASF AG)
[5])Silicone SKE Wacker
[6])Alkylated aromatic hydrocarbons (Exxon)

To widen the spectrum of action and to achieve synergistic effects, the herbicidal mixture may be mixed with a large number of representatives of other herbicidal or growth-regulating active compound groups and then applied concomitantly. Suitable co-components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-CF$_3$-phenyl derivatives, carbamates, quinolinecarboxylic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonylureas, triazines, triazinones, triazolinones, triazolcarboxamides and uracils.

It may furthermore be advantageous to apply the herbicidal mixture, alone or in combination with other herbicides, in the form of a mixture with other crop protection agents, for example with agents for controlling pests or phytopathogenic fungi or bacteria. Also of interest is the miscibility with mineral salt solutions, which are employed for treating nutritional and trace element deficiencies.

Depending on the control target, the season, the target plants and the growth stage, the application rate of the herbicidal mixture is from 0.01 to 1.0, preferably from 0.01 to 0.5, kg of active substance/ha, based on the pure components of the herbicidal mixture.

Use Example

The herbicidal action of the compositions according to the invention could be demonstrated by greenhouse experiments:

The culture containers used were plastic pots containing loamy sand with approximately 3.0% of humus as the substrate. The seeds of the test plants were sown separately for each species.

For the pre-emergence treatment, the herbicidal mixture, which had been suspended or emulsified in water, was applied directly after sowing by means of finely distributing nozzles. The containers were irrigated gently to promote germination and growth and subsequently covered with transparent plastic hoods until the plants had rooted. This cover causes uniform germination of the test plants, unless this was adversely affected by the herbicidal mixture.

For the post-emergence treatment, the test plants were first grown to a height of 3 to 15 cm, depending on the plant habit, and then treated with the herbicidal mixture which had been suspended or emulsified in water. The test plants were for this purpose either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the above-ground parts, and 0 means no damage, or normal course of growth.

The plants used for the greenhouse experiments were of the following species:

| Abbreviation | Scientific name | Common name |
|---|---|---|
| ABUTH | Abutilon theophrasti | velvet leaf |
| SETVI | Setaria viridis | green foxtail |
| SETFA | Setaria faberi | giant foxtail |

EXAMPLE 1

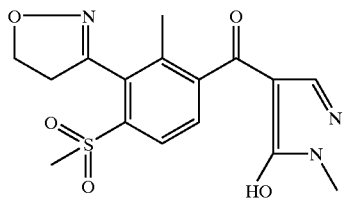

EXAMPLE 2

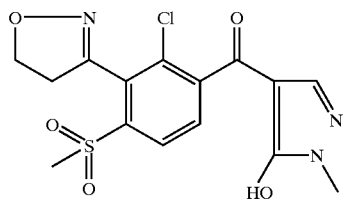

TABLE 3

Post-emergent herbicidal activity in the greenhouse

| Active compound | AWM kg of a.s./ha | Phytotoxicity SETFA | SETVI |
|---|---|---|---|
| EX. 1 | 0.05 | 91.5 | 75 |
| EX. 1 + No. 6, Table 2 | 0.05 + 0.6 | 95 | 95 |
| EX. 1 + AG 6202 + Ensol 28 | 0.05 + 0.5 + 5.0 | 85 | 95 |

TABLE 4

Post-emergent herbicidal activity in the greenhouse

| Active compound | AWM kg of a.s./ha | Phytotoxicity SETFA | SETVI | ABUTH |
|---|---|---|---|---|
| EX. 2 | 0.05 | 57.5 | 80 | 92.5 |
| EX. 2 + No. 6, Table 2 | 0.05 + 0.6 | 97.5 | 95 | 100 |
| EX. 2 + Lutensol ON 80 + Ensol 28 | 0.05 + 0.5 + 0.56 | 82.5 | 77.5 | 96.5 |
| EX. 2 + AG 6202 + Ammonium sulfate | 0.05 + 0.5 + 5.0 | 67.5 | 90 | 94 |
| EX. 2 + Atplus + Ensol 28 | 0.05 + 0.5 + 0.56 | 80 | 92.5 | 100 |

Legend for the adjuvants used:

| Name | | |
|---|---|---|
| AG ® 6202 | Akzo | alkyl glycoside APG |
| Lutensol ® ON 80 | BASF AG | alkyl ethoxylate |
| Lutensol ® ON 110 | BASF AG | alkyl ethoxylate |
| ENSOL ® 28 | BASF AG | ammonium nitrate/urea solution (28% total N) |
| Atplus | Unigema | 83% paraffin oil + 17% nonionic emulsifier |

The data from Tables 3 and 4 show unambiguously the synergistic effect of the herbicidal two-component mixture according to the invention, compared to the respective three-component mixtures and the pure active compound.

We claim:

1. A herbicidal composition comprising a) a herbicidally effective amount of a benzoyl compound of formula I

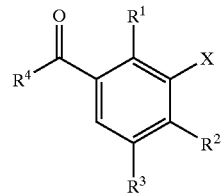

where:
R$^1$, R$^2$ are halogen, C$_1$–C$_6$-alkyl, C$_1$–C$_6$-alkylthio, C$_1$–C$_6$-alkyl-sulfinyl or C$_1$–C$_6$-alkylsulfonyl;
R$^3$ is hydrogen, halogen, C$_1$–C$_6$-alkyl;
X is 4,5-dihydroisoxazolyl which is unsubstituted or mono- or polysubstituted by halogen, C$_1$–C$_6$-alkyl, C$_1$–C$_4$-alkoxy, C$_1$–C$_4$-haloalkyl, C$_1$–C$_4$-haloalkoxy, C$_1$–C$_4$-alkylthio;
R$^4$ is a pyrazole of the formula II

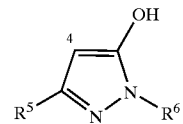

which is attached in the 4-position and where
R$^5$ is hydrogen,
R$^6$ is methyl,
or an environmentally compatible salt thereof;
b) an adjuvant comprising
  i) a C$_1$–C$_5$-alkyl C$_5$–C$_{22}$-alkanoate,
  ii) a C$_{10}$–C$_{20}$-carboxylic acid,
  iii) a partial phosphoric ester or a partial sulfuric ester of a monohydroxy-functional polyalkyl ether and
  iv) optionally an alkyl polyoxyalkylene polyether,
wherein the compound of formula I and the adjuvat are present in synergistically effective amounts.

2. The composition defined in claim 1, wherein R$^3$ is hydrogen.

3. The composition defined in claim 1, wherein X is 4,5-dihydroisoxazolyl which is unsubstituted or substituted by C$_1$–C$_6$-alkyl.

4. The composition defined in claim 3, wherein X is 4,5-dihydroisoxazole.

5. The composition defined in claim 1, wherein X is 4,5-dihydroisoxazol-3-yl, 4,5-dihydro-5-methylisoxazol-3-yl, 4,5-dihydro-5-ethylisoxazol-3-yl or 4,5-dihydro-4,5-dimethylisoxazol-3-yl.

6. The composition defined in claim 5, wherein R$^1$ is chlorine or methyl.

7. The composition defined in claim 5, wherein R$^2$ is SO$_2$CH$_3$.

8. The composition defined in claim 1, wherein the carboxylic acid is selected from the group consisting of oleic acid, palmitic acid, myristic acid, linoleic acid, linolenic acid, lauric acid and stearic acid.

9. The composition defined in claim 1, wherein the carboxylic acid is mono- or polyunsaturated.

10. The composition defined in claim 1, wherein the benzoyl compound is 4-[2-chloro-3-(4,5-dihydroisoxazol-3-yl)-4-methylsulfonylbenzoyl]-1-methyl-5-hydroxy-1H-pyrazole.

11. The composition defined in claim 1, wherein the benzoyl compound is 4-[2-methyl-3-(4,5-dihydroisoxazol-3-yl)-4-methylsulfonylbenzoyl]-1-methyl-5-hydroxy-1H-pyrazole.

12. The composition defined in claim 1, comprising 0.5–90% by weight of the benzoyl compound a) and 10–99.5% by weight of the adjuvant b).

13. The composition defined in claim 1, wherein the adjuvant b) comprises from 5 to 90% of the $C_1$–$C_5$-alkyl $C_5$–$C_{22}$-alkanoate, from 2 to 40% of the $C_{10}$–$C_{20}$-carboxylic acid, from 4 to 40% of the partial phosphoric ester or the partial sulfuric ester of a monohydroxy-functional polyalkyl ether, and from 0 to 75% of the alkyl polyoxyalkylene polyether.

14. The composition defined in claim 13, wherein the adjuvant b) comprises from 5 to 60% of the $C_1$–$C_5$-alkyl $C_5$–$C_{22}$-alkanoate, from 2 to 40% of the $C_{10}$–$C_{20}$-carboxylic acid, from 5 to 35% of the partial phosphoric ester or the partial sulfuric ester of a monohydroxy-functional polyalkyl ether, and from 0 to 70% of the alkyl polyoxyalkylene polyether.

15. The composition defined in claim 13, wherein the adjuvant b) comprises from 5 to 40% of the $C_1$–$C_5$-alkyl $C_5$–$C_{22}$-alkanoate, from 2 to 35% of the $C_{10}$–$C_{20}$-carboxylic acid, from 5 to 30% of the partial phosphoric ester or the partial sulfuric ester of a monohydroxy-functional polyalkyl ether and from 0 to 70% of the alkyl polyoxyalkylene polyether.

16. A process for preparing the composition defined in claim 1, which comprises mixing the benzoyl compound a) and the adjuvant b).

17. A method for controlling undesirable vegetation, which comprises allowing a herbicidally effective amount of the composition defined in claim 1 to act on plants or their habitat, and wherein the benzoyl compound a) and the adjuvant b) are applied separately or jointly.

18. The method of claim 17, which comprises mixing synergistically effective amounts of the benzoyl compound a) and the adjuvant b) and allowing the mixture to act on the plants or their habitat.

* * * * *

UNITED STATES PATENT AND TRADEMARK OFFICE
CERTIFICATE OF CORRECTION

PATENT NO. : 6,514,910 B1
DATED : February 4, 2003
INVENTOR(S) : Bratz et al.

Page 1 of 1

It is certified that error appears in the above-identified patent and that said Letters Patent is hereby corrected as shown below:

<u>Title page,</u>
Item [57], ABSTRACT,
Line 3, after formula I, "$C_1$-$C_6$-alkyl-sulfinyl" should be -- $C_1$-$C_6$-alkylsulfinyl --;
Line 11, after formula II, "adjuvat" should be -- adjuvant --.

<u>Column 10,</u>
Line 13, "$C_1$-$C_6$-alkyl-sulfinyl" should be -- $C_1$-$C_6$-alkylsulfinyl --.
Line 38, "adjuvat" should be -- adjuvant --.

Signed and Sealed this

Twenty-fifth Day of March, 2003

JAMES E. ROGAN
*Director of the United States Patent and Trademark Office*